United States Patent
Zamanzadeh et al.

(10) Patent No.: US 11,085,908 B1
(45) Date of Patent: Aug. 10, 2021

(54) NON-DESTRUCTIVE TESTING SYSTEM FOR DETECTING GRAPHITIZATION OF IRON

(71) Applicant: MATERGENICS, INC., Pittsburgh, PA (US)

(72) Inventors: Mehrooz Zamanzadeh, Pittsburgh, PA (US); Carolyn Tome, Pittsburgh, PA (US); Anil Kumar Chikkam, Pittsburgh, PA (US)

(73) Assignee: Matergenics, Inc., Pittsburgh, PA (US)

(\*) Notice: Subject to any disclaimer, the term of this patent is extended or adjusted under 35 U.S.C. 154(b) by 0 days.

(21) Appl. No.: 16/999,151

(22) Filed: Aug. 21, 2020

Related U.S. Application Data

(60) Provisional application No. 63/026,366, filed on May 18, 2020, provisional application No. 62/890,676, filed on Aug. 23, 2019.

(51) Int. Cl.
  *G01N 33/2028*  (2019.01)
  *G01N 17/00*    (2006.01)

(52) U.S. Cl.
  CPC ....... *G01N 33/2028* (2019.01); *G01N 17/006* (2013.01)

(58) Field of Classification Search
  CPC ... G01N 33/2028; G01N 17/006; G01N 17/04
  See application file for complete search history.

(56) References Cited

U.S. PATENT DOCUMENTS

| | | | | |
|---|---|---|---|---|
| 4,087,742 A * | 5/1978 | Khoo | ...... | C23F 13/02 |
| | | | | 204/196.07 |
| 4,488,939 A * | 12/1984 | Fu | ...... | G01N 17/02 |
| | | | | 204/404 |
| 6,946,855 B1 * | 9/2005 | Hemblade | ...... | G01N 17/04 |
| | | | | 324/700 |
| 7,719,266 B1 * | 5/2010 | Zamanzadeh | ...... | G01R 33/1223 |
| | | | | 324/240 |
| 7,912,273 B2 | 3/2011 | Survant et al. | | |
| 8,023,722 B1 | 9/2011 | Kovarik et al. | | |
| 8,154,279 B1 * | 4/2012 | Zamanzadeh | ...... | G01R 33/1223 |
| | | | | 324/240 |
| 8,280,145 B2 | 10/2012 | Kovarik et al. | | |
| 8,375,803 B2 | 2/2013 | Butterfield | | |
| 9,310,338 B2 | 4/2016 | Yarbro et al. | | |
| 9,658,297 B2 | 5/2017 | Hull et al. | | |
| 9,726,594 B2 * | 8/2017 | Jovancicevic | ...... | G01N 17/02 |
| 9,915,222 B2 | 3/2018 | Mackey et al. | | |
| 10,060,881 B2 | 8/2018 | Estevez et al. | | |
| 10,672,046 B2 | 6/2020 | Messinger et al. | | |

(Continued)

FOREIGN PATENT DOCUMENTS

AU  2011313872 B2  1/2015
CN  105181786 A    12/2015

*Primary Examiner* — Nathaniel J Kolb
(74) *Attorney, Agent, or Firm* — Thomas M. Joseph, Esq

(57) ABSTRACT

The graphitization of a sample having a sample surface and bulk material adjacent to the sample surface is determined with a housing holding a potentiometer and a processor connected to the potentiometer. The processor receives electric potential measurements from the potentiometer at the sample surface and uses the electric potential measurements to quantify the graphitization of the bulk material adjacent to the sample surface to generate graphitization data for output.

11 Claims, 10 Drawing Sheets

(56) References Cited

U.S. PATENT DOCUMENTS

| | | | |
|---|---|---|---|
| 2003/0074162 A1* | 4/2003 | Fourie | G01R 31/12 |
| | | | 702/188 |
| 2007/0017822 A1* | 1/2007 | Gill | G01N 17/02 |
| | | | 205/775.5 |
| 2008/0283418 A1* | 11/2008 | Jovancicevic | G01N 17/02 |
| | | | 205/775.5 |
| 2009/0195260 A1* | 8/2009 | Bell | G01N 17/04 |
| | | | 324/700 |
| 2012/0103104 A1 | 5/2012 | Butterfield | |
| 2014/0188649 A1 | 7/2014 | Messinger et al. | |
| 2014/0354307 A1* | 12/2014 | Clarke | G01N 27/20 |
| | | | 324/700 |
| 2015/0300990 A1 | 10/2015 | Estevez et al. | |
| 2015/0368809 A1* | 12/2015 | Atkins | C23F 13/04 |
| | | | 205/728 |
| 2016/0274060 A1* | 9/2016 | Denenberg | G01N 27/9073 |
| 2017/0176391 A1 | 6/2017 | Yu et al. | |
| 2019/0257675 A1* | 8/2019 | Lewis | G01D 21/02 |

* cited by examiner

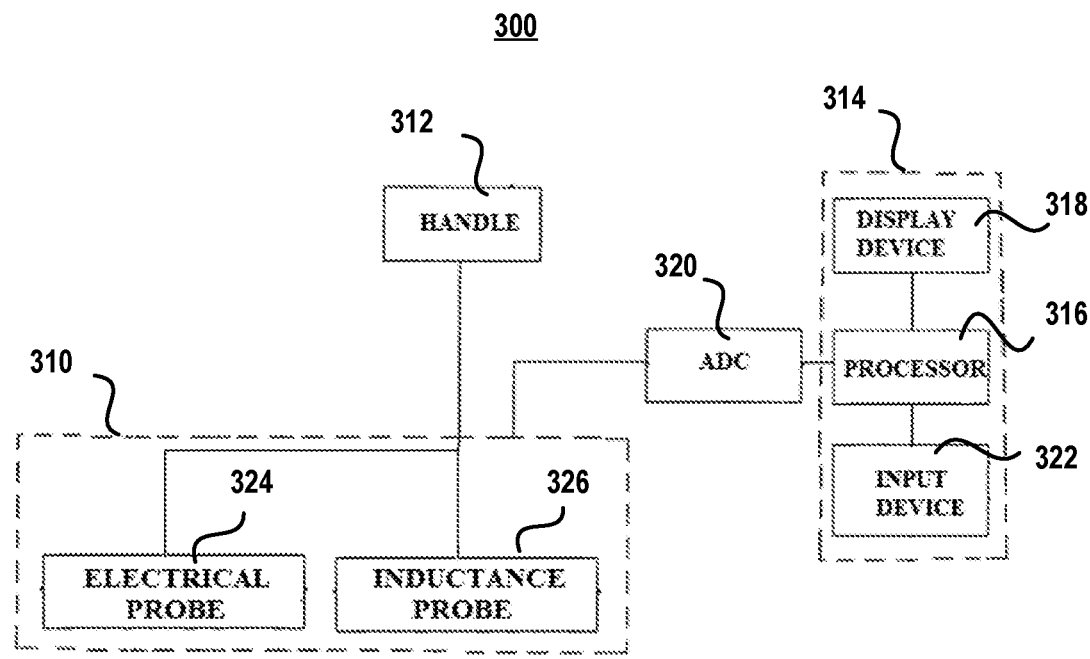
FIG. 5
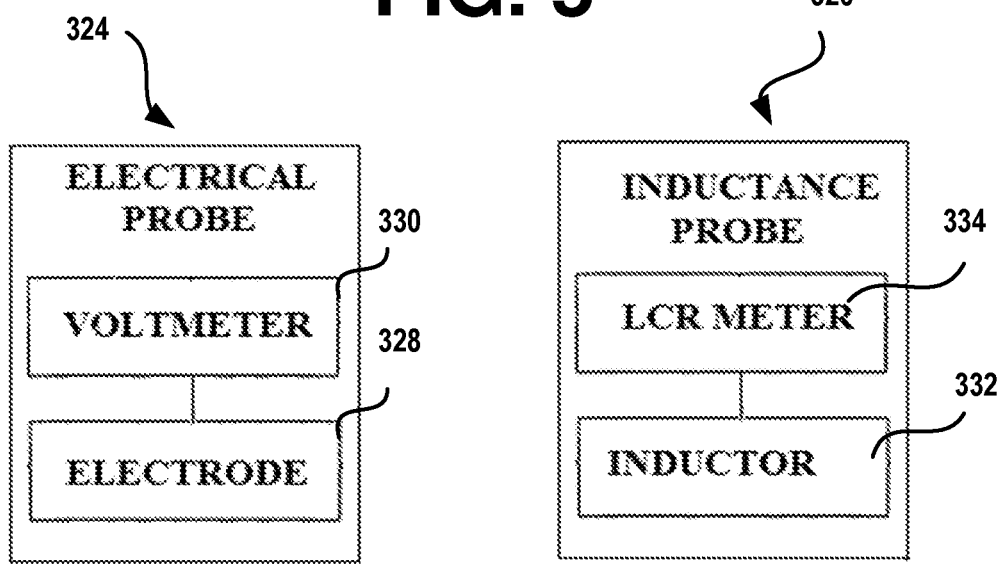
FIG. 6  FIG. 7

NON-DESTRUCTIVE TESTING SYSTEM FOR DETECTING GRAPHITIZATION OF IRON

CROSS REFERENCE TO RELATED APPLICATION

This application claims the benefit under 35 U.S.C. § 119(e) of U.S. Provisional Application No. 63/026,366 entitled "NON-DESTRUCTIVE TESTING SYSTEM FOR DETECTING GRAPHITIZATION OF IRON" filed May 18, 2020, and U.S. Provisional Application No. 62/890,676 entitled "NON-DESTRUCTIVE TESTING SYSTEM FOR DETECTING GRAPHITIZATION OF IRON" filed Aug. 23, 2019, which are incorporated herein by reference.

BACKGROUND

Water main failures are very expensive for municipalities because they typically result in expenses associated with repair costs, flood damage, and loss of revenue to affected businesses. Water main failures also interrupt the operation of vital services, such as medical care and firefighting operations. Currently, millions of dollars are spent annually by industry and by municipalities on the repair of failed components of the water distribution infrastructure, such as components that are made from gray cast iron or "gray iron" pipe.

The rate of municipal water main failure is expected to increase as the existing gray iron infrastructure continues to age. The cost of repairing damages caused by broken water mains (and subsequent flooding damage) may become an important item in many municipal budgets. The development of systems to prevent catastrophic failure of water distribution infrastructure components would result in tremendous savings.

Non-destructive testing techniques are utilized in programs that are designed to detect localized corrosion before actual failures occur. A typical program includes an identification of microstructure (gray iron, ductile iron, or other), an identification of corrosion mechanisms, a determination of the extent of internal and external corrosion (maximum and minimum wall thickness), a determination of degradation and distribution of the magnetic properties of the metal, and an analysis of data and determination of preventative action. The monitoring of pipe corrosion can be continued for a few years beyond the application of corrosion control and/or mitigation measures.

The metallurgy of gray iron is well understood. The most important elements in gray iron, aside from iron, are carbon and silicon. The silicon content affects the carbon distribution in the metal. Unlike the carbon in ductile iron and steel, which is disbursed as graphite spheroids and pearlite, respectively, the carbon in gray iron is present in flake form. These flakes form in the eutectic cell boundaries during cooling of the cast metal. The resulting graphite flakes form a continuous matrix throughout the gray iron.

A gray iron sample that includes an increased amount of silicon will have a decreased amount of carbon in the eutectic phase. Such a sample will have an increased amount of carbon in the form of pearlite and a decreased amount of graphite flakes. The lower content of graphite flakes results in an increase in tensile strength.

Typically, gray iron component failure is attributed to graphitic corrosion or graphitization. Graphitization occurs when the metallic constituents of gray iron are selectively removed or converted into corrosion products. Graphitization leaves behind the graphite matrix of the gray iron in the shape of the original casting. Graphitic corrosion is particularly insidious because graphitized pipe may appear perfectly sound upon visual inspection despite being embrittled and prone to premature failure under load.

Graphitic corrosion is one example of the dealloying of a metal. During dealloying, one component of an alloy is selectively dissolved, leaving other components behind. The preferential attack on iron in gray iron results from the fact that graphite is located at a highly noble or corrosion resistant position in the galvanic activity series. The relative position of two metals in the galvanic activity series determines which will most readily participate in electrochemical reactions, such as corrosion.

Pipes that are subject to graphitization may appear sound and may conduct water adequately. However, the metallic portion of a pipe wall may be significantly thinner in various places along the wall. Graphitized regions of the pipe wall will be brittle and subject to failure under load as the result of temperature variation, heavy traffic, or shock.

The galvanizing of iron with zinc inhibits corrosion because iron is nobler in the activity series than zinc. Therefore, the zinc plating layer is preferentially attacked, greatly extending the service life of the iron substrate.

Similarly, graphite is far more noble than iron, so that the graphite matrix within the gray iron can act as the cathode in an electrochemical reaction under the right conditions of soil composition and moisture. The iron in gray iron samples that are subject to an electrochemical reaction will undergo anodic attack. In such samples, the graphite matrix will survive, while the iron is dissolved away.

The properties of iron that could be used to detect graphitization or other localized corrosion phenomena include ductility, electrical resistivity, or acoustic properties, such as ultrasonic sound velocity or attenuation. However, assessing ductility, by nature, involves destruction of the sample. Acoustical methods cannot be used with coated pipes due to the fact that it requires surface contact with bare, clean metal.

The use of eddy currents to measure the electrical resistivity of a sample surface has been disclosed. Eddy current methods require sophisticated control circuitry and precisely tuned components. An eddy current device necessarily consumes a considerable amount of power to generate the radio frequency (RF) that it uses to induce eddy currents in the sample.

Ultrasonic measurement of acoustic properties requires a very clean interface between the probe and the pipe for purposes of acoustic transmission and impedance matching, so that it is poorly suited for use with exposed, buried pipe that is often wet or dirty.

Other techniques have involved the sensing of magnetic properties. Such techniques have utilized a non-destructive testing device for detecting graphitization and localized corrosion in gray cast iron, ductile iron, ferrous alloys and other magnetic materials that is based on magnetic force or magnetic flux density measurements.

While these techniques provide some insight into the degree of graphitization that has occurred in water main pipes and other similar structures, these techniques can be improved. Accordingly, there is a need for an improved non-destructive testing system for detecting the graphitization of gray iron.

SUMMARY

The following summary is provided to introduce a selection of concepts in a simplified form that are further described below in the detailed description. This summary is not intended to identify key features or essential features of the claimed subject matter, nor is it intended to be used to limit the scope of the claimed subject matter.

In various implementations, a non-destructive testing apparatus for determining the graphitization of a sample having a sample surface and bulk material adjacent to the sample surface is provided. The apparatus includes a housing holding a potentiometer and a processor connected to the potentiometer. The processor receives electric potential measurements from the potentiometer at the sample surface and uses the electric potential measurements to quantify the graphitization of the bulk material adjacent to the sample surface to generate graphitization data for output.

In other implementations, a method for detecting the graphitization of an iron sample is provided. A plurality of electric potential measurements on the surface of the iron sample surface are obtained with a potentiometer. Each of the plurality of electric potential measurements is compared to a calibration standard to quantify the graphitization of the iron sample as graphitization data. Output is generated relating to graphitization data that has been obtained for the iron sample.

These and other features and advantages will be apparent from a reading of the following detailed description and a review of the appended drawings. It is to be understood that the foregoing summary, the following detailed description and the appended drawings are explanatory only and are not restrictive of various aspects as claimed.

BRIEF DESCRIPTION OF THE DRAWINGS

FIG. 5 is a box diagram of another embodiment of a non-destructive testing system in accordance with the subject matter of this disclosure.

FIG. 6 is a box diagram of an embodiment of an electrical probe that is used with the non-destructive testing system disclosed in FIG. 5.

FIG. 7 is a box diagram of an embodiment of an inductance probe that is used with the non-destructive testing system disclosed in FIG. 5.

DETAILED DESCRIPTION

Figure 1:
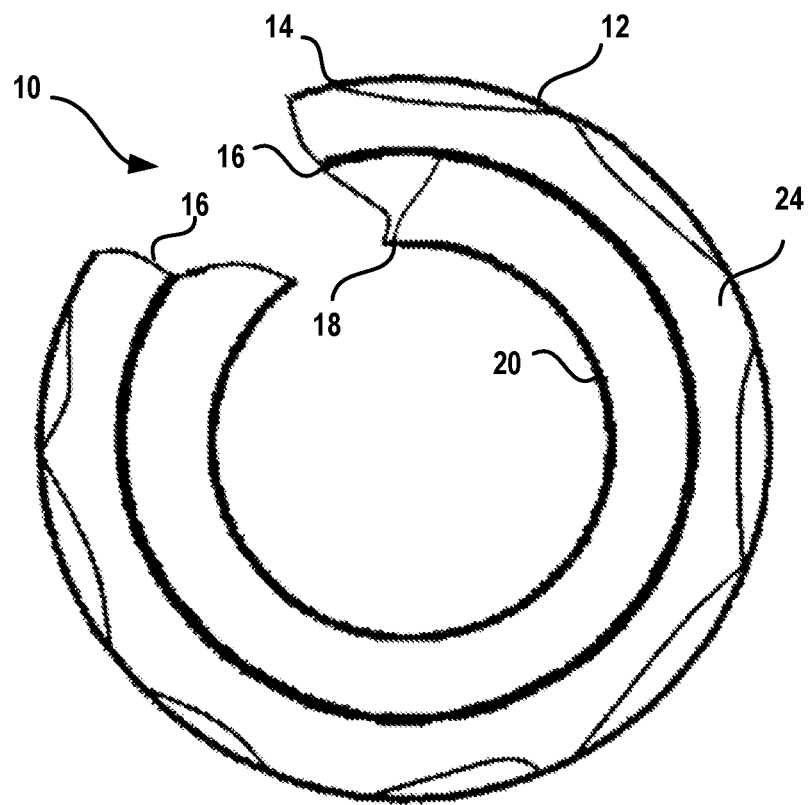
FIG. 1 is an elevational view of the cross section of a graphitized pipe sample.

The subject disclosure is directed to systems, methods, and apparatus for relating electric potential measurements to graphitization and, more particularly, to a non-destructive testing device for detecting graphitization and localized corrosion in gray cast iron, ductile iron, ferrous alloys and other magnetic materials based on electric potential measurements. The non-destructive testing device is an improvement to non-destructive testing devices that are based on magnetic force or magnetic flux density measurements.

The subject disclosure includes a simple apparatus and method for measuring graphitization and, more particularly, to a simple non-destructive testing device for detecting graphitization and localized corrosion in gray cast iron, ductile iron, ferrous alloys and other magnetic materials. The non-destructive testing device is intended to be used in field inspections of water main pipes and similar structures without disrupting their operation.

The detailed description provided below in connection with the appended drawings is intended as a description of examples and is not intended to represent the only forms in which the present examples can be constructed or utilized. The description sets forth functions of the examples and sequences of steps for constructing and operating the examples. However, the same or equivalent functions and sequences can be accomplished by different examples.

References to "one embodiment," "an embodiment," "an example embodiment," "one implementation," "an implementation," "one example," "an example" and the like, indicate that the described embodiment, implementation or example can include a particular feature, structure or characteristic, but every embodiment, implementation or example can not necessarily include the particular feature, structure or characteristic. Moreover, such phrases are not necessarily referring to the same embodiment, implementation or example. Further, when a particular feature, structure or characteristic is described in connection with an embodiment, implementation or example, it is to be appreciated that such feature, structure or characteristic can be implemented in connection with other embodiments, implementations or examples whether or not explicitly described.

Numerous specific details are set forth in order to provide a thorough understanding of one or more embodiments of the described subject matter. It is to be appreciated, however, that such embodiments can be practiced without these specific details.

Various features of the subject disclosure are now described in more detail with reference to the drawings, wherein like numerals generally refer to like or corresponding elements throughout. The drawings and detailed description are not intended to limit the claimed subject matter to the particular form described. Rather, the intention is to cover all modifications, equivalents and alternatives falling within the spirit and scope of the claimed subject matter.

The subject disclosure is directed to non-destructive testing devices that rely upon measurements electric potential to detect graphitization of ferrous alloys, particularly gray iron or ductile iron. The invention is also suitable for detecting other types of localized corrosion phenomena in such samples, as well as localized corrosion phenomena in other materials that include magnetic components. Embodiments of the non-destructive testing devices can be implemented in conjunction with or as part of the disclosed non-destructive testing devices that measure the interaction of magnetic fields with sample surfaces that include magnetic materials set forth in U.S. Pat. No. 8,154,279 to Zamanzadeh et. al.

Figure 2:
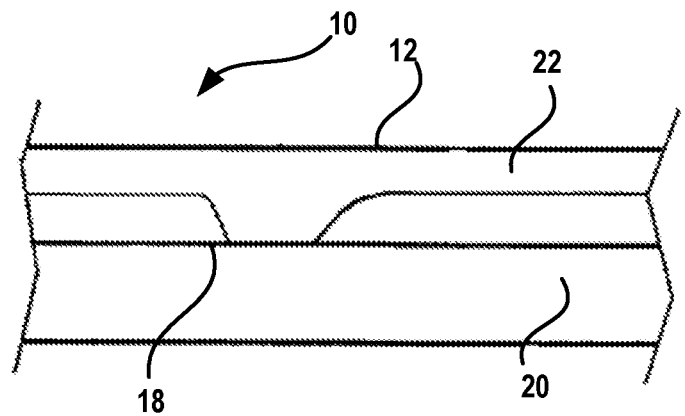
FIG. 2 is a fragmentary elevational view of the cross section of the graphitized pipe sample shown in FIG. 1.

Referring now to FIGS. 1-2, there is illustrated a schematic diagram of an exemplary graphitized pipe, generally designated by the numeral 10. The graphitized pipe 10 corresponds to the gray cast iron sample disclosed in U.S. Pat. No. 8,154,279 to Zamanzadeh et. al. The gray cast iron sample 10 was taken from a water main structure that fractured after being subjected to graphitization corrosion. Chemical analysis of the sample indicated the presence of carbon (3.11 wt %), manganese (0.39 wt %), phosphorus (0.39 wt %), sulfur (0.073 wt %), and silicon (1.59 wt %) in quantities that met the chemical requirements for gray cast iron alloys that are used in pipe applications.

Visual inspection of the sample 10 revealed primary and secondary cracks on an outside surface 12 of the pipe sample 10. A crack 14 initiated at the outside surface 12 and propagated inward, resulting in a longitudinal fracture 16. The Brinell hardness of the pipe 10 was 83.5 HB. The hardness near the fracture 16 measured 82 HB. The pipe 10 met the Talbot test (modulus of rupture and secant modulus of elasticity) requirements for gray cast iron.

An inside surface 18 of the pipe 10 included a continuous cement coating 20. The coating 20 was strongly adherent to the surface 18 and did not include any evidence of corrosion. Micrographs revealed a carbon distribution consistent with ASTM standards for gray iron, with graphite, ferrite, and pearlite visible. The graphite was of ASTM A247 type B. The soil (not shown) above and below the failed pipe 10 had a measured resistivity of 1100 to 2300 ohm-cm.

Similar pipes that were used in under similar conditions experienced an increasing failure rate over time. This increase in failure rate is typical of a piping system undergoing corrosion. The failures could not be attributed to brittleness, alone, so that graphitization corrosion and wall thinning was suspected. The observed failures included longitudinal fractures that occurred when such pipes were subjected to a crushing load at locations weakened by graphitization.

Visual observation, optical microscopy, and EDS (energy dispersive x-ray spectroscopy for analysis of chemical composition) microanalysis showed localized corrosion 22 on the exterior surface 12 of the pipe 10. Examination of the internal surface 18 showed no signs of either localized or uniform corrosion. Metallographic examination of the cross section showed the characteristic appearance of localized graphitization 22 with 25% penetration of the pipe wall.

Figure 3:
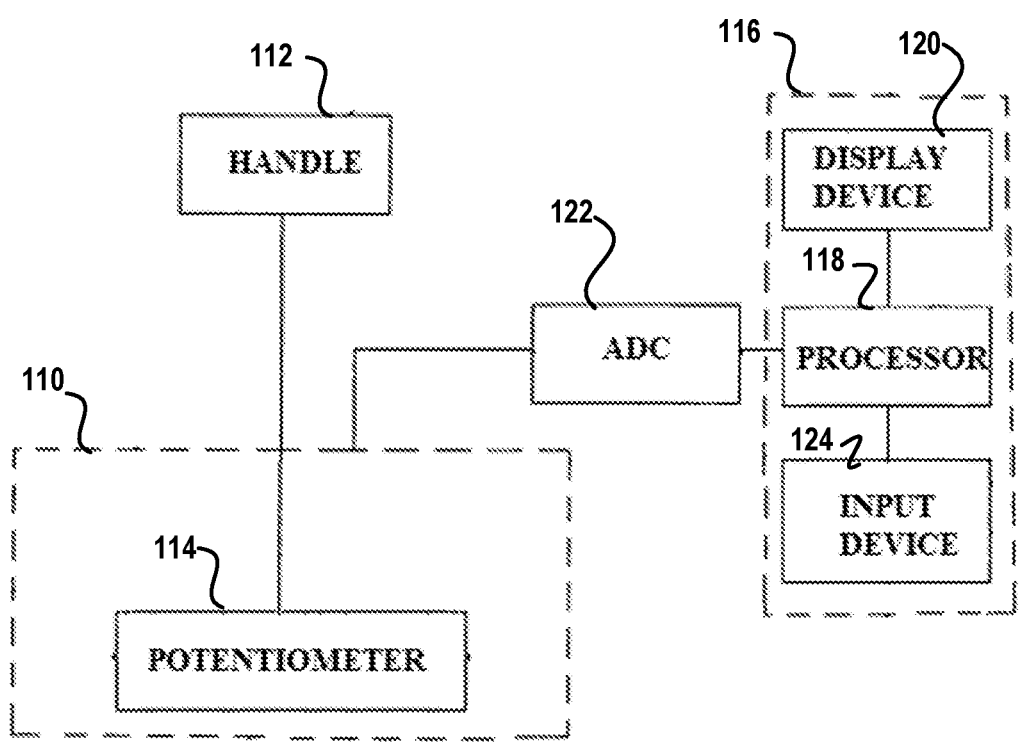
FIG. 3 is a box diagram of a non-destructive testing system in accordance with the subject matter of this disclosure.

Referring now to FIGS. 1-3, a non-destructive testing apparatus, generally designated by the numeral 100, for testing the sample 10 is shown. The non-destructive testing apparatus 100 has the ability to determine the amount of graphitization or localized corrosion that has occurred in the sample 10. The apparatus 100 determines the amount of graphitization that has occurred in the iron sample 10 by measuring the electric potential at various points along the outside surface 12 of the sample 10.

The electric potential at any point along the outside surface 12 corresponds the amount of graphitization that has occurred within the adjacent bulk material of the sample. Unlike conventional systems that measure graphitization or corrosion, including systems that measure the interaction of magnetic fields with sample surfaces that include magnetic materials, the non-destructive testing apparatus 100 can utilize electrical potential measurements to determine the depth of graphitization.

In some embodiments, the non-destructive testing apparatus 100 can be implemented as a stand-alone device that is using in conjunction with the non-destructive testing devices disclosed in U.S. Pat. No. 8,154,279 to Zamanzadeh et. al. In other embodiments, the non-destructive testing apparatus 100 can be implemented as a component of a non-destructive testing system that includes one of the non-destructive testing devices disclosed in U.S. Pat. No. 8,154,279 to Zamanzadeh et. al.

Iron is selectively removed through corrosion in a typical sample surface 10. The corroded sample surface 10 includes graphitized areas 22 of gray iron that exhibit distinctive electric potential measurements that correlate to the amount of graphitization that has occurred.

As shown in FIG. 3, the apparatus 100 includes a tubular housing or wand 110 and a handle 112. The handle 112 extends from the housing 110 to facilitate manual manipulation, mechanical manipulation, and/or electro-mechanical manipulation to allow the measurement of the corrosion by measuring electric potential at various locations along the sample outside surface 12. The housing 110 holds a potentiometer 114.

The housing 110 and the handle 112 are made from any suitable materials by any suitable manufacturing process. Preferably, the housing 110 and the handle 112 are made from non-ferrous materials.

As shown in FIGS. 1-3, the potentiometer 114 interacts with the sample outside surface 12 when the housing 110 is positioned in close proximity (e.g., less than 1 cm) to the sample 10. The potentiometer 114 transmits the electric potential measurements at various points along the outside surface 12 to computer system 116 that includes a processor 118, which processes the electric potential measurements for display on a display device 120.

The computer system 116 is a suitable microcontroller, laptop computer, personal computer, network computer, or other computing device. The computer system 116 utilizes the processor 118 to implement custom software to perform data collection, potentiometer monitoring, and user interface functions. The potentiometer 114 transfers measurement data to the processor 118 through an analog-to-digital converter (ADC) 122. The computer system 116 can include an internal memory device (not shown).

The computer system 116 has the ability to receive input through a keypad or other input device 124 for processing by the processor 118. The processor 118 also has the ability to send output to the display device 120. The processor 118 converts the electric potential measurements into a suitable data structure or form for output to the display device 120. In some embodiments, the form is a map illustrating point measurements or regions having electric potentials that correspond to the amount of graphitization that has occurred within the sample 10.

The processor 118 receives data from the potentiometer 114. The data is displayed on the display device 120 in its raw form or is used to calculate the amount of graphitization that has occurred within the sample 10 in appropriate units. The processor 118 sends the electric potential data to the display device 120 for output and, optionally, to a storage device (not shown) for logging.

As illustrated in FIGS. 1-3, the handle 112 is used to move the housing 110 relative to the sample 10 to allow the potentiometer 114 to take measurements at a plurality of locations along the sample outside surface 12. The processor 118 receives the measurements from the potentiometer 114 and uses the measurements to determine the electric potential of the sample outside surface 12 at each location. The processor 118 uses the electric potential measurements to generate a map of the graphitization of the sample 10 for output to the display device 120.

Figure 4:
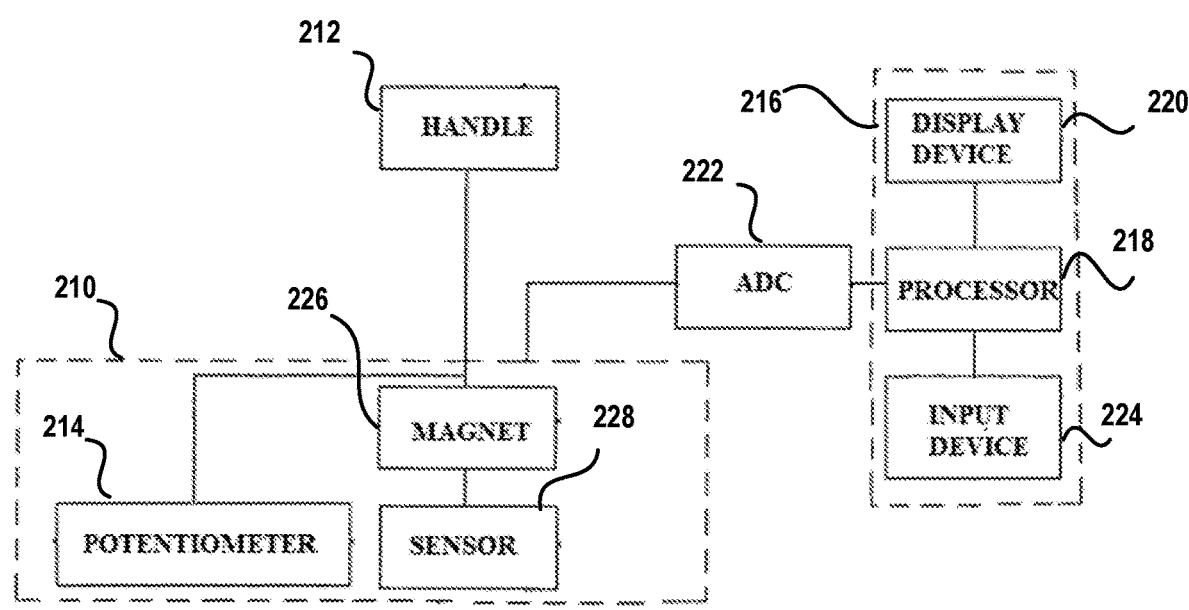
FIG. 4 is a box diagram of another embodiment of a non-destructive testing system in accordance with the subject matter of this disclosure.

Referring now to FIG. 4 with continuing reference to the foregoing figures, another embodiment of a non-destructive testing apparatus, generally designated by the numeral 200, is shown. The non-destructive testing apparatus 200 is implemented with the non-destructive testing devices disclosed in U.S. Pat. No. 8,154,279 to Zamanzadeh et. al.

Like the embodiment shown in FIG. 3, the non-destructive testing apparatus 200 includes a tubular housing or wand 210, a handle 212, a potentiometer 214, a computer system 216, a processor 218, a display device 220, an ADC 222, and an input device 224. The processor 218 receives electric potential measurements from the potentiometer 214 at a sample surface, such as the sample outside surface 12 shown in FIGS. 1-2. The processor 218 uses the electric potential measurements to quantify the graphitization of the bulk material adjacent to the sample outside surface 12 to generate graphitization data for output on the display device 220.

Unlike the embodiment shown in FIG. 3, the non-destructive testing apparatus 200 includes a magnet 226 that functions as a magnetic field generator and a sensor 228. The magnet 226 can be any suitable magnet, such as a permanent magnet or an electromagnet.

The magnet 226 generates a magnetic field to interact with the sample outside surface 12 shown in FIGS. 1-2. The sensor 228 obtains magnetic property measurements based upon the interaction of the magnetic field with the sample outside surface 12. The magnetic property measurements can include magnetic permeability measurements, magnetic force measurements, and/or magnetic flux density measurements.

The sensor 228 sends the magnetic property measurements through the ADC 222 to the processor 218 to refine the output for the display device 220. In some embodiments, the sensor 228 can include a strain gauge assembly having a cantilever having the ability to deflect when interacting with the sample surface and a strain gauge for measuring the deflection of the cantilever. The strain gauge assembly can be similar to the embodiment shown in FIG. 3 of U.S. Pat. No. 8,154,279 to Zamanzadeh et. al.

In other embodiments, the sensor 228 can be implemented as a magnetic flux density sensor, such as Hall effect sensors, giant magneto resistance (GMR) sensors, sense coils, pickup coils, optical sensors based upon the Faraday effect, and other flux density sensing sensors. The sensor 228 is a Hall effect sensor that is affixed to the tip of housing 210 and is aligned with the pole of the magnet 226 in an orientation that facilitates measurement of the magnetic field parallel to the axis of the magnet 226.

The potentiometer 214 can cooperate with the sensor 226 to provide measurements that can be used to generate a map of the outside surface of a sample, such as the outside surface 12 of the iron sample 10 shown in FIGS. 1-2. The potentiometer 214 can obtain electric potential measurements at a plurality of locations along the sample outside surface 12. The sensor 226 can obtain magnetic property measurements at a plurality of locations along the sample outside surface 12.

The processor 218 can utilize the electric potential measurements to generate output for the display device 220. The processor 218 can utilize the magnetic property measurements to refine the output. The output can be formatted for display as a map. The display device 220 can render the formatted output for display as a map.

Referring now to FIGS. 5-7 with continuing reference to the foregoing figures, another embodiment of a non-destructive testing apparatus, generally designated by the numeral 300, is shown. Like the embodiments shown in FIGS. 3-4, the non-destructive testing apparatus 300 includes a tubular housing or wand 310, a handle 312, a computer system 314, a processor 316, a display device 318, an ADC 320, and an input device 322.

Unlike the embodiments shown in FIGS. 3-4, the apparatus 300 includes an electrical probe 324 and an inductance probe 326. The electrical probe 324 includes a reference electrode 328 that can measure a voltage that can be read by a voltmeter 330. The inductance probe 326 includes an inductor 332 and an LCR meter 334 that can measure the inductance of the inductor 332. In some embodiments, the electrical probe 324 can be the potentiometer 114 shown in FIG. 3. In other embodiments, the electrical probe 324 and the inductance probe 326 are separated, physically, in different housings or tubular members. In yet other embodiments, the non-destructive testing apparatus 300 can include either an electrical probe 324 or an inductance probe 326, so that the non-destructive testing apparatus 300 can measure only certain electrical properties of samples or only inductance.

The LCR meter 334 can measure the inductance of the inductor 332. The processor 316 communicates with the LCR meter 334 to receive inductance measurements therefrom. The processor 316 uses the inductance measurements to quantify the graphitization of the bulk material adjacent to a sample surface, such as the outer surface 12 shown in FIG. 1, to generate graphitization data for output on the display device 318. In some embodiments, the electrical probe 324 measures the potential difference of a portion of the outer surface 12 to determine whether the portion includes graphitization.

The electrical probe 324 and the inductance probe 326 are used in series. The electrical probe 324 can be used to locate graphitization either on a sample surface or below a sample surface. The inductance probe 326 can be used to confirm that graphitization has occurred and to determine how much graphitization is present.

The electrode 328 can be placed in electrical contact with a sample surface, such as the outer surface 12 shown in FIG. 1, through physical contact or through immersion in a shallow aqueous solution that has the ability to conduct electricity. The electrical contact can complete an electrical circuit that has a predetermined voltage. In some embodiments, the voltage ranges from 1-3 volts, so that the electrical probe 324 has a resolution of +/−10 millivolts. In other embodiments, the voltmeter 330 can be a high impedance voltmeter.

In some embodiments, the electrical probe 324 can be used to identify particular metals or alloys, such as copper, zinc, stainless steel, galvanized steel, cast iron, because individual elements have signature electrical potentials. For example, zinc, platinum, graphite, and iron have electrical potentials of −1 volt, 0.1 volts, 0.2 volts, and 0.4 volts, respectively. The ability to detect elements can be enhanced by adding copper sulfate to the aqueous solution.

The inductance probe 326 can detect the amount of graphitization of a graphitized pipe, such as the graphitized pipe 10 shown in FIGS. 1-2, by the change in inductance of the inductor 332. The inductor 332 can be a small inductor that includes a ferrite material core that has a 3 mm diameter and a 25 mm length. The inductor 332 can be wound with two to four layers of agnet wire. The approximate inductance of the inductor 332 in open air (far away from any magnetic material) is 3 mH.

In operation, the coil is oriented 90 degrees to the outer surface 12 with one end of the coil positioned at a distance of approximately 0.040 inches from the outer surface 12. As the inductor 332 is moved over a non-graphitized area of the pipe, such as the area 24 shown in FIG. 1, the measured inductance will increase because the flux produced by the coil will be partially absorbed by the iron in the graphitized pipe 10. As the inductor 332 is moved over an area containing graphitization, the measured inductance will decrease because there is less iron to absorb the flux. The measured inductance of the inductor 332 will be in proportion to the geometry of the graphitized area. The coil is made to be as small as possible to increase the detection sensitivity.

Typically, the inductance of an inductor is measured by supplying a known current or voltage and frequency to the inductor and detecting the relationship between the voltage, current, and phase. The applied signal and resultant magnetic flux is in the form of a sine wave with a frequency of in this case 1 kHz. The LCR meter 334, which is a standard LCR meter, can be used to measure the inductance.

In some embodiments, eddy current losses can be associated with the flux absorption. In such embodiments, the eddy current losses can be measured to detect non-ferrous metals, such as brass and aluminum. Such embodiments can be used to detect corrosion on non-ferrous pipes. Eddy current measurements are not as sensitive to changes in graphitization, as compared to measuring inductance directly.

Figure 8:
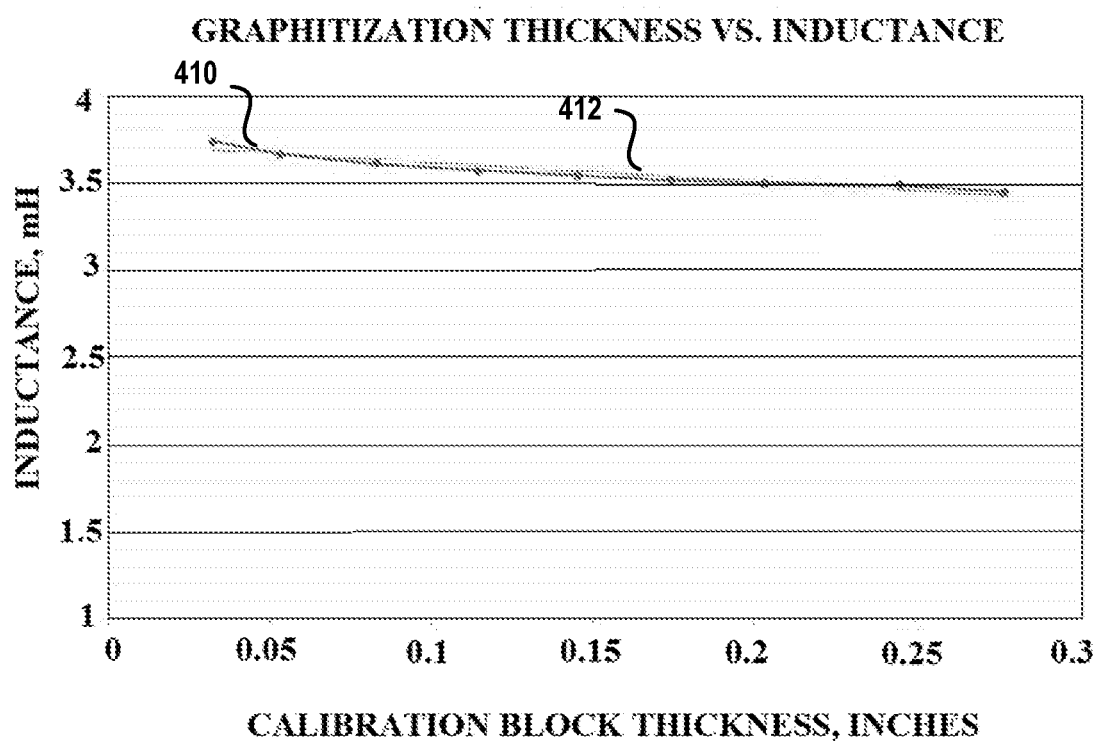
FIG. 8 is a plot of the relationship between graphitization thickness and inductance.

Referring now to FIG. 8 with continuing reference to the foregoing figures, a plot, generally designated by the numeral 400, illustrates the relationship between sample thickness and inductance is shown. The inductance can be measured with an inductance probe, such as the inductance probe 326 shown in FIGS. 5 and 7. The plot 400 illustrates the comparison of actual measurements 410 with a straight line 412, which demonstrates that the relationship is approximately linear within the range of about 0 inches to about 0.3 inches in sample thickness.

In some embodiments, the ability of the inductance probe 326 to measure graphitization is limited to graphitization that is no more than 0.4 inches below a surface. Additionally, the ability of the inductance probe 326 to measure inductance can be sensitive to surface irregularities or excessively rough surfaces. In such embodiments, the functionality of the inductance probe 326 can be enhanced with the ability to detect slight misalignments with sample surfaces through the use of v-shaped probe surface, multiple coils, or optical detectors that ensure that the inductance probe 326 maintains contact with the surface and/or that the sample surface is essentially flat.

Figure 9:
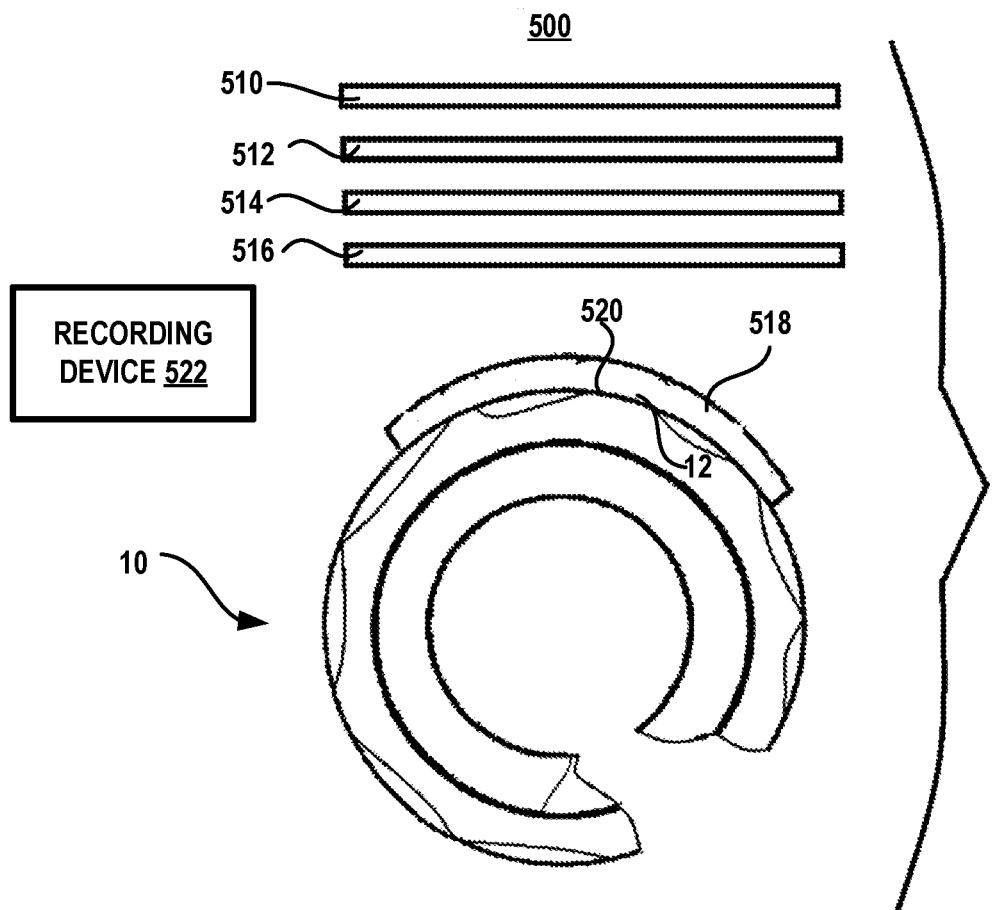
FIG. 9 is a schematic diagram of a non-destructive testing apparatus in accordance with the subject matter of this disclosure.

Referring now to FIGS. 1-2 and 9 with continuing reference to the foregoing figures, a non-destructive testing apparatus, generally designated by the numeral 500, for testing the sample 10 is shown. The non-destructive testing apparatus 500 has the ability to estimate the amount of graphitization or localized corrosion that has occurred in the sample 10. The apparatus 500 determines the amount of graphitization that has occurred in the iron sample 10 by utilizing a plurality of flexible magnetic strips 510-518 that include varying amounts of magnetic materials and/or varying magnetic properties.

The apparatus 500 is particularly adapted for estimating the amount of graphitization that is present in samples, like the sample 10, in a remote and/or an outdoor environment. The apparatus 500 can be provided in the form of a kit for field testing. The apparatus 500 is portable, lightweight, and economical. Additionally, the apparatus 500 is simple to operate.

Each one of the flexible magnetic strips 510-518 has the ability to provide a magnetic field having a predetermined strength. The strength of the magnetic field can be correlated with the amount of graphitization that has occurred in the sample 10 by placing one of the flexible magnetic strips 510-518, in series, in close proximity to the outside surface 12.

If the amount of graphitization in the sample 10 exceeds a predetermined level, one or more of the flexible magnetic strips 510-518 will not be magnetically attracted to the sample 10. The amount of graphitization in the sample 10 can be estimated by determining, which, if any, of the flexible magnetic strips 510-518 is magnetically attracted to the sample 10.

Each one of the flexible magnetic strips 510-518 has sufficient flexibility to conform to the outside surface 12 of the sample 10. As shown in FIG. 9, an engaging surface 520 of the flexible magnetic strip 518 conforms to the outside surface 12 when the flexible magnetic strip 518 is placed in contact with the sample 10. If the amount of graphitization in the sample 10 does not exceed a predetermined level, the flexible magnetic strip engaging surface 520 will become fixedly attached to the outer surface 12 due to the magnetic attraction between the flexible magnetic strip 518 and the sample 10.

Each one of the flexible magnetic strips 510-518 includes flexible material and permanent magnetic material. The amount of flexible material will depend upon the amount of flexibility that each one of the flexible magnetic strips 510-518 will need to be sufficiently flexible to conform to the outside surface 12 of the sample 10. The amount of permanent magnetic material will depend upon the strength of the magnetic field that will need to be produced by each one of the flexible magnetic strips 510-518. In some embodiments, each of one of the flexible magnetic strips 510-518 will include a different amount of permanent magnetic material.

The flexible material can be any suitable material that has sufficient flexibility to conform to the outer surface 12. Suitable materials can include metals, plastics, and/or composites. The permanent magnetic material can include any suitable ferromagnetic material, including iron alloys, nickel alloys, cobalt alloys, rare-earth metal alloys, and minerals, like lodestone. In some embodiments, the permanent magnetic material can be the flexible material.

The outer surface 12 can have any shape or profile. In some embodiments, the outer surface 12 has a curved or arcuate profile. In other embodiments, the outer surface 12 is substantially circular, elliptical, or circular.

In some embodiments, the apparatus 500 can include a recording device 522 for recording the test results and/or an estimate of the graphitization of the sample 10. The recording device 522 can be a mechanical device, an electronic device, or a combination thereof. Electronic devices can include one or more computers or computing devices and one or more memory devices. Electronic devices can be digital devices or analogy devices. The recording device 522 can record text, images, audio, video, or a combination thereof. In this exemplary embodiment, the recording device 522 is a pen and paper.

Figure 10:
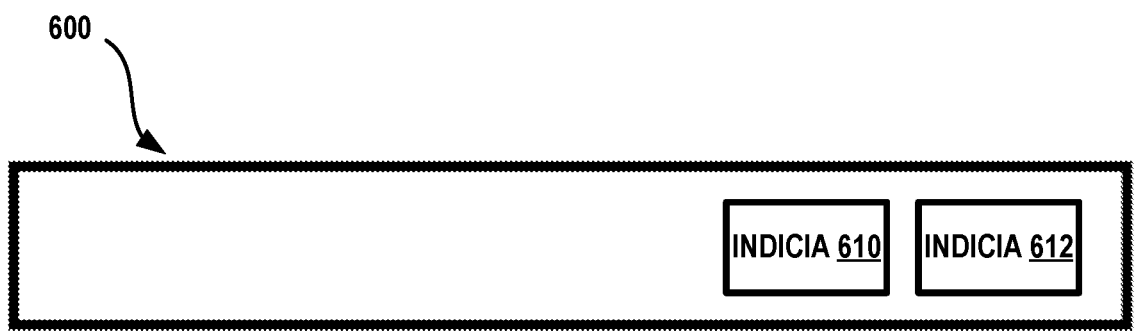
FIG. 10 is a schematic diagram of a flexible magnetic strip in accordance with the subject matter of this disclosure.

Referring now to FIG. 10 with continuing reference to the previous figures, there is shown another embodiment of a flexible magnetic strip, generally designated with the numeral 600. The flexible magnetic strip 600 can be used in place of any one or more of the flexible magnetic strips 510-518 shown in FIG. 9. The flexible magnetic strip 600 will have the same magnetic properties and mechanical properties of the one or more flexible magnetic strips 510-518 that it replaces.

Unlike the embodiment shown in FIG. 10, the flexible magnetic strip 600 include indicia 610 that indicates the amount of permanent magnetic material that is contained therein. Additionally, the flexible magnetic strip 600 includes indicia 612 that indicates the maximum amount of graphitization that can be present in the sample 10 shown in FIGS. 1-2 and 9 before the flexible magnetic strip 600 will not be magnetically attracted to the sample 10. As a result, the indicia 612 provides an estimate of the amount of graphitization or localized corrosion that has occurred in the sample 10.

Exemplary Processes

Figure 11:
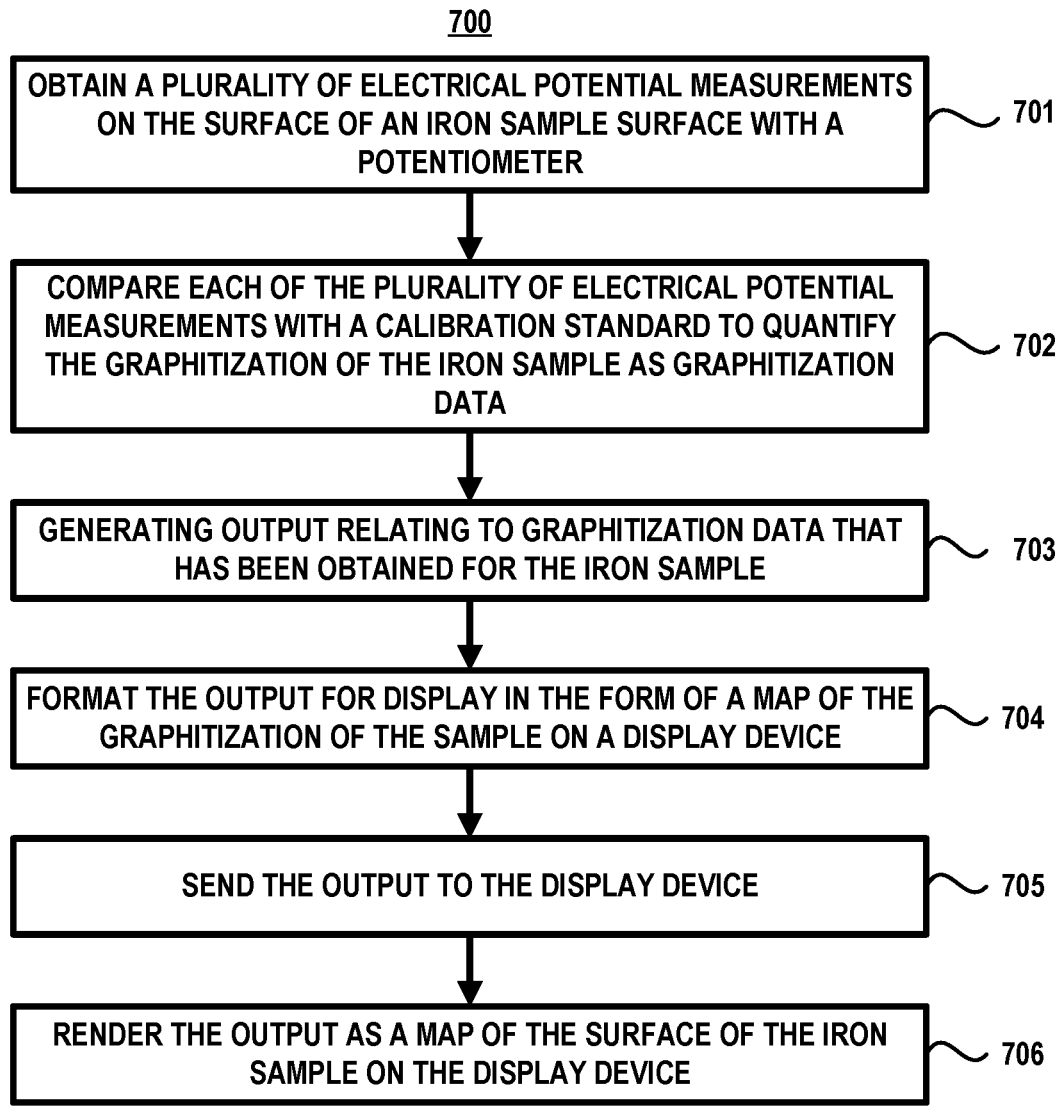
FIG. 11 is an exemplary process in accordance with the subject disclosure.

Referring now to FIG. 11 with continuing reference to the foregoing figures, an exemplary method, generally designated with the numeral 700, for detecting the graphitization of an iron sample. In this exemplary embodiment, the method 700 can be performed using the non-destructive testing apparatus 100 shown in FIG. 3 and/or the non-destructive testing apparatus shown in FIG. 4.

At 701, plurality of electric potential measurements are obtained on the surface of the iron sample surface with a potentiometer. In this exemplary embodiment, the iron sample surface can be the outer surface 12 of the iron sample 10 shown in FIGS. 1-2. The potentiometer can be the potentiometer 114 shown in FIG. 3 and/or the potentiometer 214 shown in FIG. 4.

In other embodiments, an inductor is placed in proximity to a surface of the iron sample. The change in inductance of the inductor is measured. In such exemplary embodiments, the inductor can be the inductor 332 shown in FIG. 7.

At 702, each of the plurality of electric potential measurements is compared to a calibration standard to quantify the graphitization of the iron sample as graphitization data. In this exemplary embodiment, a processor, such as the processor 118 shown in FIG. 3 and/or the processor 218 shown in FIG. 4 can compare the electric potential measurements to the calibration standard.

In other embodiments, the change in inductance of an inductor can be compared to a calibration standard to quantify the graphitization of the iron sample as graphitization data. In such exemplary embodiments, the inductor can be the inductor 332 shown in FIG. 7.

At 703, output relating to graphitization data that has been obtained for the iron sample is generated. In this exemplary embodiment, the processor 118 shown in FIG. 3 and/or the processor 218 shown in FIG. 4 can generate the output. In embodiments that include an inductor, the processor can be the processor 316 shown in FIG. 5.

At 704, the output is formatted for display in the form of a map of the graphitization of the sample on the display device. In this exemplary embodiment, the processor 118 shown in FIG. 3 and/or the processor 218 shown in FIG. 4 can format the output. In embodiments that include an inductor, the processor that produces the output can be the processor 316 shown in FIG. 5.

At 705, the output is sent to a display device. In this exemplary embodiment, the display device can be the display device 120 shown in FIG. 3 and/or the display device 220 shown in FIG. 4. In embodiments that include an inductor, the display device can be the display device 318 shown in FIG. 5.

At 706, the output is rendered as a map of the surface of the iron sample on the display device. In this exemplary embodiment, the output can be rendered by the computer system 116 shown in FIG. 3 and/or the computer system 216 shown in FIG. 4. In embodiments that include an inductor, the computer system can be the computer system 314 shown in FIG. 5.

Figure 12:
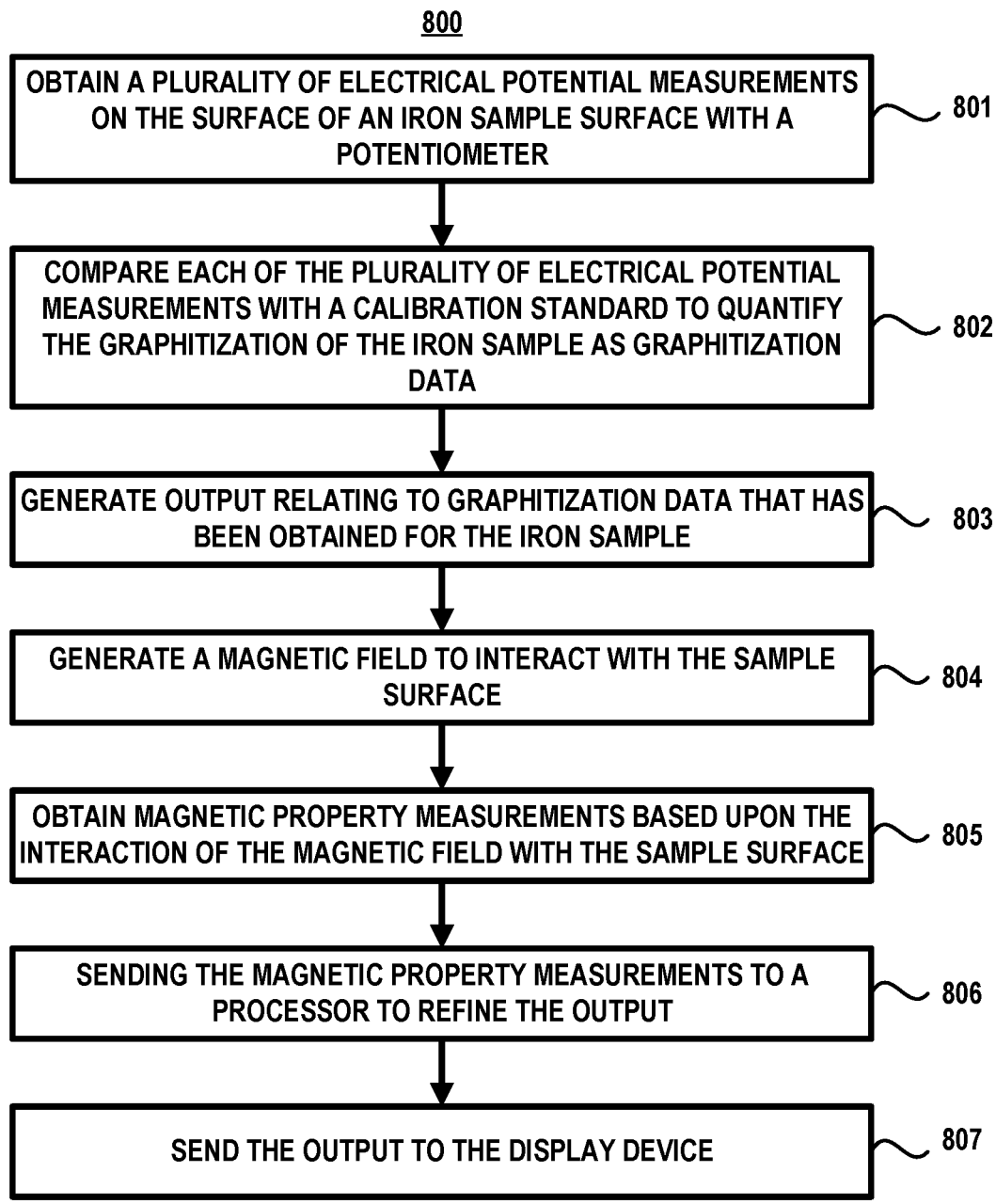
FIG. 12 is an exemplary process in accordance with the subject disclosure.

Referring now to FIG. 12 with continuing reference to the foregoing figures, another exemplary method, generally designated with the numeral 800, for detecting the graphitization of an iron sample. In this exemplary embodiment, the method 800 can be performed using the non-destructive testing apparatus shown in FIG. 4.

At 801, plurality of electric potential measurements are obtained on the surface of the iron sample surface with a potentiometer. In this exemplary embodiment, the iron sample surface can be the outer surface 12 of the iron sample 10 shown in FIGS. 1-2. The potentiometer can be the potentiometer 214 shown in FIG. 4.

At 802, each of the plurality of electric potential measurements is compared to a calibration standard to quantify the graphitization of the iron sample as graphitization data. In this exemplary embodiment, a processor, such as the processor 218 shown in FIG. 4 can compare the electric potential measurements to the calibration standard.

At 803, output relating to graphitization data that has been obtained for the iron sample is generated. In this exemplary embodiment, the processor 218 shown in FIG. 4 can generate the output.

At 804, a magnetic field is generated to interact with the sample surface. In this exemplary embodiment, the magnet 226 shown in FIG. 4 can generate the magnetic field.

At 805, magnetic property measurements based upon the interaction of the magnetic field with the sample surface are obtained. In this exemplary embodiment, the sensor 228 shown in FIG. 4 can obtain the magnetic property measurements.

At 806, the magnetic property measurements are sent to a processor to refine the output. In this exemplary embodiment, the processor 218 shown in FIG. 4 can refine the output.

At 807, the output is sent to a display device. In this exemplary embodiment, the display device can be the display device 220 shown in FIG. 4.

Figure 13:
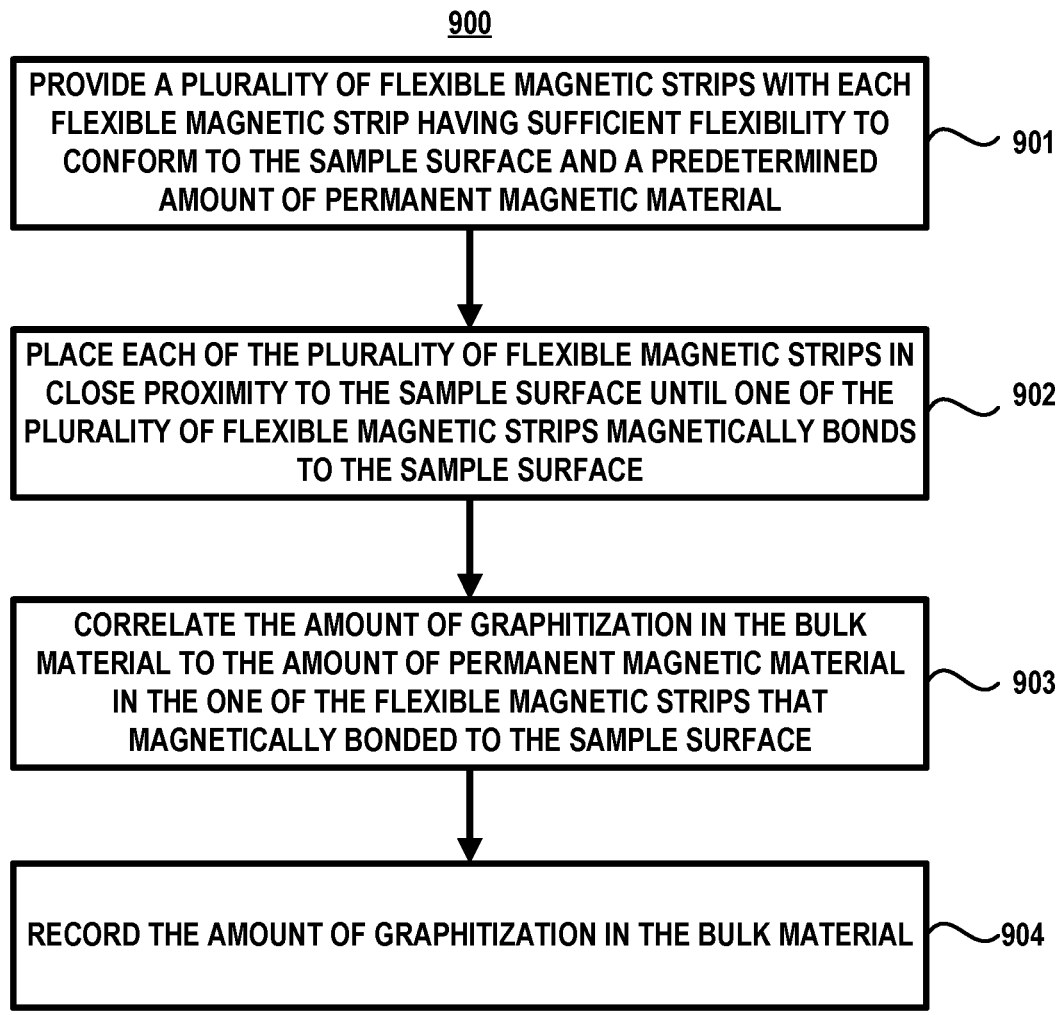
FIG. 13 is an exemplary process in accordance with the subject disclosure.

Referring now to FIG. 13 with continuing reference to the foregoing figures, an exemplary method, generally designated with the numeral 900, for detecting the graphitization of an iron sample. In this exemplary embodiment, the method 900 can be performed using the non-destructive testing apparatus 500 shown in FIG. 9 whether that apparatus 500 includes the flexible magnetic strips 510-518 shown in FIG. 9 and/or the flexible magnetic strip 600 shown in FIG. 10.

At 901, a plurality of flexible magnetic strips is provided with each flexible magnetic strip having sufficient flexibility to conform to a sample surface and a predetermined amount of permanent magnetic material. In this exemplary embodiment, the flexible magnetic strips can include the flexible magnetic strips 510-518 shown in FIG. 9 and/or the flexible magnetic strip 600 shown in FIG. 10.

At 902, each of the plurality of flexible magnetic strips is placed in close proximity to the sample surface until one of the plurality of flexible magnetic strips magnetically bonds to the sample surface. In this exemplary embodiment, the sample surface can be the sample outer surface 12 shown in FIGS. 1-2 and 9.

At 903, the amount of graphitization in the bulk material is correlated to the amount of permanent magnetic material in the one of the flexible magnetic strips that magnetically bonded to the sample surface. In this exemplary embodiment, the bulk material can be bulk material within the sample 10 shown in FIGS. 1-2 and 9.

At 904, the amount of graphitization in the bulk material is recorded. In this exemplary embodiment, the amount of graphitization is recorded with the recording device 522 shown in FIG. 9. In some embodiments, the amount of graphitization can be determined by using indicia, such as indicia 610 and/or indicia 612 shown in FIG. 10.

Exemplary Computer Systems

Figure 14:
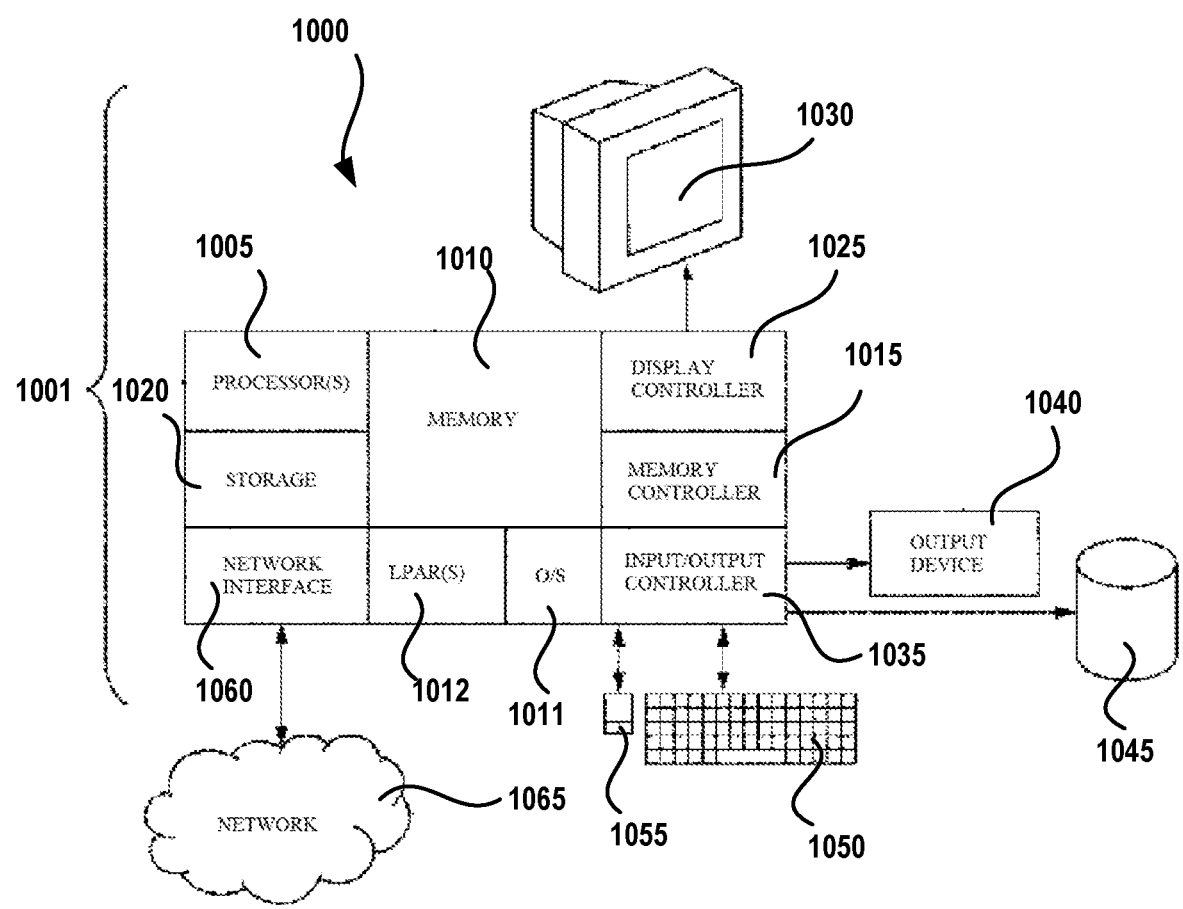
FIG. 14 is a schematic diagram for a computer system for implementing the subject matter of the subject disclosure.

Referring now to FIG. 14 with continuing reference to the forgoing figures, a computer system for generating and displaying output for a non-destructive testing system is generally shown according to one or more embodiments. The non-destructive testing system is particularly adapted for detecting the graphitization of an iron sample.

The methods described herein can be implemented in hardware, software (e.g., firmware), or a combination thereof. In an exemplary embodiment, the methods described herein are implemented in hardware as part of the microprocessor of a special or general-purpose digital computer, such as a personal computer, workstation, minicomputer, or mainframe computer. The system 1000 therefore can include general-purpose computer or mainframe 1001 capable of running multiple instances of an O/S simultaneously.

In an exemplary embodiment, in terms of hardware architecture, as shown in FIG. 14, the computer 1001 includes one or more processors 1005, memory 1010 coupled to a memory controller 1015, and one or more input and/or output (I/O) devices 1040, 1045 (or peripherals) that are communicatively coupled via a local input/output controller 1035. The input/output controller 1035 can be, for example but not limited to, one or more buses or other wired or wireless connections, as is known in the art. The input/output controller 1035 can have additional elements, which are omitted for simplicity, such as controllers, buffers (caches), drivers, repeaters, and receivers, to enable communications. Further, the local interface can include address, control, and/or data connections to enable appropriate communications among the aforementioned components. The input/output controller 1035 can include a plurality of sub-channels configured to access the output devices 1040 and 1045. The sub-channels can include fiber-optic communications ports.

The processor 1005 is a hardware device for executing software, particularly that stored in storage 1020, such as cache storage, or memory 1010. The processor 1005 can be any custom made or commercially available processor, a central processing unit (CPU), an auxiliary processor among several processors associated with the computer 1001, a semiconductor based microprocessor (in the form of a microchip or chip set), a macroprocessor, or generally any device for executing instructions.

The memory 1010 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 1010 can incorporate electronic, magnetic, optical, and/or other types of storage media. Note that the memory 1010 can have a distributed architecture, where various components are situated remote from one another, but can be accessed by the processor 1005.

The instructions in memory 1010 can include one or more separate programs, each of which comprises an ordered listing of executable instructions for implementing logical functions. In the example of FIG. 14, the instructions in the memory 1010 a suitable operating system (OS) 1011. The operating system 1011 essentially controls the execution of other computer programs and provides scheduling, input-output control, file and data management, memory management, and communication control and related services.

The memory 1010 can include multiple logical partitions (LPARs) 1012, each running an instance of an operating system. The LPARs 1012 can be managed by a hypervisor, which can be a program stored in memory 1010 and executed by the processor 1005.

In an exemplary embodiment, a conventional keyboard 1050 and mouse 1055 can be coupled to the input/output controller 1035. Other output devices such as the I/O devices 1040, 1045 can include input devices, for example but not limited to a printer, a scanner, microphone, and the like. Finally, the I/O devices 1040, 1045 can further include devices that communicate both inputs and outputs, for instance but not limited to, a network interface card (NIC) or modulator/demodulator (for accessing other files, devices, systems, or a network), a radio frequency (RF) or other transceiver, a telephonic interface, a bridge, a router, and the like. The system 1000 can further include a display controller 1025 coupled to a display 1030. In an exemplary embodiment, the system 1000 can further include a network interface 1060 for coupling to a network 1065. The network 1065 can be an IP-based network for communication between the computer 1001 and any external server, client and the like via a broadband connection. The network 1065 transmits and receives data between the computer 1001 and external systems. In an exemplary embodiment, network 1065 can be a managed IP network administered by a service provider. The network 1065 can be implemented in a wireless fashion, e.g., using wireless protocols and technologies, such as WiFi, WiMax, etc. The network 1065 can also be a packet-switched network such as a local area network, wide area network, metropolitan area network, Internet network, or other similar type of network environment. The network 1065 can be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 1001 is a PC, workstation, intelligent device or the like, the instructions in the memory 1010 can further include a basic input output system (BIOS) (omitted for simplicity). The BIOS is a set of essential software routines that initialize and test hardware at startup, start the OS 1011, and support the transfer of data among the hardware devices. The BIOS is stored in ROM so that the BIOS can be executed when the computer 1001 is activated.

When the computer 1001 is in operation, the processor 1005 is configured to execute instructions stored within the memory 1010, to communicate data to and from the memory 1010, and to generally control operations of the computer 1001 pursuant to the instructions.

In accordance with one or more embodiments described herein, the computer 1001 can implement and/or perform the disclosed subject matter. As shown, computer 1001 can include instructions in memory 1010 for performing and/or controlling Steps 701-706 shown in FIG. 11 and/or Steps 801-807 shown in FIG. 12. The computer system 116 shown in FIG. 3 can be implemented as the computer 1001 shown in FIG. 14 with the display device 120 being implemented as the display 1030 shown in FIG. 14. The computer system 216 shown in FIG. 4 can be implemented as the computer 1001 shown in FIG. 14 with the display device 220 being implemented as the display 1030 shown in FIG. 14. The computer system 314 shown in FIG. 5 can be implemented as the computer 1001 shown in FIG. 14 with the display device 318 being implemented as the display 1030 shown in FIG. 14.

The disclosed subject matter can be implemented as a system, a method, and/or a computer program product at any possible technical detail level of integration. The computer program product can include a computer readable storage medium (or media) having computer readable program instructions thereon for causing a processor to carry out embodiments and features of the subject disclosure. Additionally, the system can be implemented within a cloud environment.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to exploit features of the present disclosure.

Embodiments and features of the subject disclosure are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the subject disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Supported Features and Embodiments

The detailed description provided above in connection with the appended drawings explicitly describes and supports various features of apparatus and methods for detecting graphitization in samples. By way of illustration and not limitation, supported embodiments include a non-destructive testing apparatus for determining the graphitization of a sample having a sample surface and bulk material adjacent to the sample surface, the apparatus comprising: a housing holding a potentiometer, and a processor connected to the potentiometer, wherein the processor receives electric potential measurements from the potentiometer at the sample surface and uses the electric potential measurements to quantify the graphitization of the bulk material adjacent to the sample surface to generate graphitization data for output.

Supported embodiments include the foregoing non-destructive testing apparatus, wherein the potentiometer is in close proximity to the sample surface.

Supported embodiments include any of the foregoing non-destructive testing apparatus, further comprising: a handle connected to the housing.

Supported embodiments include any of the foregoing non-destructive testing apparatus, further comprising: a display device for receiving output from the processor.

Supported embodiments include any of the foregoing non-destructive testing apparatus, wherein the processor formats the electric potential measurements to generate output in the form of a map of the graphitization of the sample on the display device.

Supported embodiments include any of the foregoing non-destructive testing apparatus, wherein the sample is made from material selected from the group consisting of gray iron, gray cast iron, and ductile iron.

Supported embodiments include any of the foregoing non-destructive testing apparatus, further comprising: a sensor, and a magnetic field generator, wherein the generator generates a magnetic field to interact with the sample surface and the sensor obtains magnetic property measurements based upon the interaction of the magnetic field with the sample surface, and the processor receives the magnetic property measurements from the sensor to refine the graphitization data for output.

Supported embodiments include any of the foregoing non-destructive testing apparatus, wherein the sensor measures at least one of magnetic permeability, magnetic force, and magnetic flux density.

Supported embodiments include any of the foregoing non-destructive testing apparatus, wherein the sensor includes a strain gauge assembly having a cantilever having the ability to deflect when interacting with the sample surface and a strain gauge for measuring the deflection of the cantilever.

Supported embodiments include any of the foregoing non-destructive testing apparatus, wherein the sensor is a magnetic flux density sensor selected from the group consisting of Hall effect sensors, magneto resistance sensors, pickup coils, and optical sensors.

Supported embodiments include any of the foregoing non-destructive testing apparatus, wherein the magnetic field generator is in close proximity to the sample surface.

Supported embodiments include any of the foregoing non-destructive testing apparatus, wherein the magnetic field generator includes at least one of a permanent magnet and an electromagnet.

Supported embodiments include any of the foregoing non-destructive testing apparatus, wherein the sensor obtains magnetic property measurements and the potentiometer obtains electric potential measurements at a plurality of locations along the sample surface, and the processor receives the magnetic property measurements and the electric potential measurements to generate a map of the graphitization of the sample for output.

Supported embodiments include a kit, a method, a system, and/or means for implementing any of the foregoing non-destructive testing apparatus or a portion thereof.

Supported embodiments include a method for detecting the graphitization of an iron sample comprising: obtaining a plurality of electric potential measurements on the surface of the iron sample surface with a potentiometer, comparing each of the plurality of electric potential measurements to a calibration standard to quantify the graphitization of the iron sample as graphitization data, and generating output relating to graphitization data that has been obtained for the iron sample.

Supported embodiments include the foregoing method, further comprising: sending the output to a display device.

Supported embodiments include any of the foregoing methods, further comprising: formatting the output for display in the form of a map of the graphitization of the sample on the display device.

Supported embodiments include any of the foregoing methods, further comprising: rendering the output as a map of the surface of the iron sample on the display device.

Supported embodiments include any of the foregoing methods, further comprising: generating a magnetic field to interact with the sample surface, obtaining magnetic property measurements based upon the interaction of the magnetic field with the sample surface, and sending the magnetic property measurements to a processor to refine the output.

Supported embodiments include any of the foregoing methods, further comprising: sending the output to a display device.

Supported embodiments include any of the foregoing methods, comprising: formatting the output for display in the form of a map of the graphitization of the sample on the display device.

Supported embodiments include any of the foregoing methods, further comprising: rendering the output as a map of the surface of the iron sample on the display device.

Supported embodiments include a system, a kit, an apparatus, and/or means for implementing any of the foregoing methods or a portion thereof.

Supported embodiments include a non-destructive testing apparatus for determining the graphitization of a pipe having a sample surface and bulk material adjacent to the sample surface, the apparatus comprising: a plurality of flexible magnetic strips with each flexible magnetic strip having sufficient flexibility to conform to the sample surface, wherein each flexible magnetic strip has a predetermined amount of permanent magnetic material so that the flexible magnetic strip will magnetically bond to the sample surface when the amount of graphitization of the bulk material is below a predetermined level.

Supported embodiments include the foregoing non-destructive testing apparatus, wherein each flexible magnetic strip has a different amount of permanent magnetic material.

Supported embodiments include any of the foregoing non-destructive testing apparatus, wherein each flexible magnetic strip includes indicia indicating the amount of permanent magnetic material therein.

Supported embodiments include any of the foregoing non-destructive testing apparatus, wherein each flexible magnetic strip includes indicia indicating the predetermined level of graphitization in the bulk material.

Supported embodiments include any of the foregoing non-destructive testing apparatus, wherein the sample surface is curved.

Supported embodiments include any of the foregoing non-destructive testing apparatus, wherein the pipe has an arcuate profile.

Supported embodiments include any of the foregoing non-destructive testing apparatus, further comprising a recording device for recording the amount of graphitization of the bulk material.

Supported embodiments include a kit, a method, a system, and/or means for implementing any of the foregoing non-destructive testing apparatus or a portion thereof.

Supported embodiments include a method for determining the graphitization of a pipe having a sample surface and bulk material adjacent to the sample surface comprising: providing a plurality of flexible magnetic strips with each flexible magnetic strip having sufficient flexibility to conform to the sample surface and a predetermined amount of permanent magnetic material, and placing each of the plurality of flexible magnetic strips in close proximity to the sample surface until one of the plurality of flexible magnetic strips magnetically bonds to the sample surface.

Supported embodiments include the foregoing method, further comprising: correlating the amount of graphitization in the bulk material to the amount of permanent magnetic material in the one of the flexible magnetic strips that magnetically bonded to the sample surface.

Supported embodiments include any of the foregoing methods, further comprising: recording the amount of graphitization in the bulk material that bonds to the sample surface.

Supported embodiments include any of the foregoing methods, wherein each flexible magnetic strip has a different amount of permanent magnetic material.

Supported embodiments include any of the foregoing methods, wherein each flexible magnetic strip includes indicia indicating the amount of permanent magnetic material therein.

Supported embodiments include any of the foregoing methods, wherein each flexible magnetic strip includes indicia indicating the predetermined level of graphitization in the bulk material.

Supported embodiments include any of the foregoing methods, wherein the sample surface is curved.

Supported embodiments include any of the foregoing methods, wherein the pipe has an arcuate profile.

Supported embodiments include a system, a kit, an apparatus, and/or means for implementing any of the foregoing methods or a portion thereof.

Supported embodiments include a kit for determining the graphitization of a pipe having a sample surface and bulk material adjacent to the sample surface, the kit comprising: a plurality of flexible magnetic strips with each flexible magnetic strip having sufficient flexibility to conform to the sample surface, wherein each flexible magnetic strip has a predetermined amount of permanent magnetic material so that the flexible magnetic strip will magnetically bond to the sample surface when the amount of graphitization of the bulk material is below a predetermined level.

Supported embodiments include the foregoing kit, wherein each flexible magnetic strip has a different amount of permanent magnetic material.

Supported embodiments include any of the foregoing kits, wherein each flexible magnetic strip includes indicia indicating the amount of permanent magnetic material therein.

Supported embodiments include any of the foregoing kits, wherein each flexible magnetic strip includes indicia indicating the predetermined level of graphitization in the bulk material.

Supported embodiments include any of the foregoing kits, wherein the sample surface is curved.

Supported embodiments include any of the foregoing kits, wherein the pipe has a circular profile.

Supported embodiments include any of the foregoing kits, further comprising a recording device for recording the amount of graphitization of the bulk material.

Supported embodiments include a system, a method, an apparatus, and/or means for implementing any of the foregoing kits or a portion thereof.

Supported embodiments include a non-destructive testing apparatus for determining the graphitization of a sample having a sample surface and bulk material adjacent to the sample surface, the apparatus comprising: an inductance probe having an inductor and a meter for measuring the inductance of the inductor, and a processor communicating with the meter, wherein the processor receives inductance measurements from the meter and uses the inductance measurements to quantify the graphitization of the bulk material adjacent to the sample surface to generate graphitization data for output.

Supported embodiments include the foregoing non-destructive testing apparatus, wherein the inductor is in close proximity to the sample surface.

Supported embodiments include any of the foregoing non-destructive testing apparatuses, further comprising: a housing holding the inductance probe.

Supported embodiments include any of the foregoing non-destructive testing apparatuses, further comprising: a handle connected to the housing.

Supported embodiments include any of the foregoing non-destructive testing apparatuses, further comprising: a display device for receiving output from the processor.

Supported embodiments include any of the foregoing non-destructive testing apparatuses, wherein the processor formats the inductance measurements to generate output in the form of a map of the graphitization of the sample on the display device.

Supported embodiments include any of the foregoing non-destructive testing apparatuses, wherein the sample is made from material selected from the group consisting of gray iron, gray cast iron, and ductile iron.

Supported embodiments include any of the foregoing non-destructive testing apparatuses, further comprising: an electrical probe for measuring the potential difference of a portion of the sample surface, wherein the electrical probe identifies a portion of the sample surface that includes a predetermined amount of graphitization and the inductance probe quantifies the amount of graphitization of the portion of the sample surface.

Supported embodiments include a kit, a method, a system, and/or means for implementing any of the foregoing non-destructive testing apparatus or a portion thereof.

Supported embodiments include a method for detecting the graphitization of an iron sample comprising: placing an inductor in proximity to a surface of the iron sample, measuring the change in inductance of the inductor, comparing the change in inductance to a calibration standard to quantify the graphitization of the iron sample as graphitization data, and generating output relating to graphitization data that has been obtained for the iron sample.

Supported embodiments include the foregoing method, further comprising: sending the output to a display device.

Supported embodiments include any of the foregoing methods, further comprising: formatting the output for display in the form of a map of the graphitization of the sample on the display device.

Supported embodiments include any of the foregoing methods, further comprising: rendering the output as a map of the surface of the iron sample on the display device.

Supported embodiments include any of the foregoing methods, further comprising: positioning an electrical probe in proximity to the iron sample surface to identify a portion of the iron sample surface that includes a predetermined amount of graphitization, and determining the amount of graphitization of the portion of the iron sample surface with the inductor.

Supported embodiments include a system, a kit, an apparatus, and/or means for implementing any of the foregoing methods or a portion thereof.

Supported embodiments can provide various attendant and/or technical advantages in terms of providing a non-destructive testing device that measures graphitization in gray iron, ductile cast iron, ferrous alloys, and other magnetic materials. Supported embodiments include such a non-destructive testing device that utilizes a potentiometer and/or a potentiometer in combination with a system that measures the interaction of a magnetic field generator with an iron sample surface.

Supported embodiments include a non-destructive testing device for preventing water main failures. The device can be implemented as part of a program that can include various protection strategies, such as cathodic protection strategies, coatings, backfill, and replacement. Such embodiments can provide long-term corrosion mitigation and maintenance that effectively extends the life of the water lines and prevents failures. The strategies can be based on test results, scheduled maintenance, and maintenance that has been performed already.

Supported embodiments includes a simple non-destructive testing device that measures graphitization in gray iron, ductile cast iron, ferrous alloys, and other magnetic materials. Supported embodiments include such a non-destructive testing device that utilizes a plurality of flexible magnetic strips that include varying amounts of magnetic material, so that the strength of the magnetic field that is produce correlates with the amount of graphitization in a sample.

Supported embodiments include a non-destructive testing device for preventing water main failures. The device can be implemented as part of a program that can include various protection strategies, such as cathodic protection strategies, coatings, backfill, and replacement. Such embodiments can provide long-term corrosion mitigation and maintenance that effectively extends the life of the water lines and prevents failures. The strategies can be based on test results, scheduled maintenance, and maintenance that has been performed already.

The detailed description provided above in connection with the appended drawings is intended as a description of examples and is not intended to represent the only forms in which the present examples can be constructed or utilized.

It is to be understood that the configurations and/or approaches described herein are exemplary in nature, and that the described embodiments, implementations and/or examples are not to be considered in a limiting sense, because numerous variations are possible.

The specific processes or methods described herein can represent one or more of any number of processing strategies. As such, various operations illustrated and/or described can be performed in the sequence illustrated and/or described, in other sequences, in parallel, or omitted. Likewise, the order of the above-described processes can be changed.

Although the subject matter has been described in language specific to structural features and/or methodological acts, it is to be understood that the subject matter defined in the appended claims is not necessarily limited to the specific features or acts described above. Rather, the specific features and acts described above are presented as example forms of implementing the claims.

What is claimed is:

1. A method for detecting the graphitization of an iron sample comprising:
    contacting a probe with a surface of the iron sample at various points to obtain a plurality of signature electrical potential measurements using a potentiometer,
    comparing each of the plurality of signature electrical potential measurements to a calibration standard to quantify the graphitization of the iron sample as graphitization data, and
    generating output relating to graphitization data that has been obtained for the iron sample,
    wherein the signature electrical potentials are generated by electrochemical reactions in the iron sample.

2. The method of claim 1, further comprising:
    sending the output to a display device.

3. The method of claim 2, further comprising:
    formatting the output for display in the form of a map of the graphitization of the sample on the display device.

4. The method of claim 2, further comprising:
    rendering the output as a map of the surface of the iron sample on the display device.

5. The method of claim 1, further comprising:
    generating a magnetic field to interact with the sample surface,
    obtaining magnetic property measurements based upon the interaction of the magnetic field with the sample surface, and
    sending the magnetic property measurements to a processor to refine the output.

6. The method of claim 5, further comprising:
    sending the output to a display device.

7. The method of claim 6, further comprising:
    formatting the output for display in the form of a map of the graphitization of the sample on the display device; and
    rendering the output as a map of the surface of the iron sample on the display device.

8. The method of claim 1, wherein the probe includes a reference electrode.

9. A method for identifying and quantifying the graphitization of an iron sample comprising:
identifying graphitization of the iron sample by:
contacting a probe with a surface of the iron sample at various points to obtain a plurality of signature electrical potential measurements using a potentiometer; and
comparing the signature electric potential measurements to a calibration standard to identify the presence of graphitization at the various points of the iron sample; and
quantifying the identified points of graphitization of the iron sample by:
generating a magnetic field to interact with the iron sample;
obtaining inductance measurements based upon the interaction of the magnetic field with the iron sample; and
comparing the inductance measurements to a calibration standard to quantify the graphitization the iron sample,
wherein the signature electrical potentials are generated by electrochemical reactions in the iron sample.

10. The method of claim 9, wherein the probe includes a reference electrode.

11. The method of claim 9, wherein the iron sample is made from a material selected from the group consisting of gray iron, gray cast iron, and ductile iron.

\* \* \* \* \*